US011571509B2

(12) United States Patent  (10) Patent No.: US 11,571,509 B2
Verlaak et al.  (45) Date of Patent: Feb. 7, 2023

(54) MEDICAMENT DELIVERY DEVICE

(71) Applicant: Sanofi-Aventis Deutschland GMBH, Frankfurt am Main (DE)

(72) Inventors: Stefan Verlaak, Paderno d'Adda (IT); Ilario Melzi, Milan (IT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1027 days.

(21) Appl. No.: 16/321,734

(22) PCT Filed: Jul. 28, 2017

(86) PCT No.: PCT/EP2017/069135
§ 371 (c)(1),
(2) Date: Jan. 29, 2019

(87) PCT Pub. No.: WO2018/024625
PCT Pub. Date: Feb. 8, 2018

(65) Prior Publication Data
US 2019/0160225 A1   May 30, 2019

(30) Foreign Application Priority Data

Aug. 2, 2016  (EP) ................................. 16182306

(51) Int. Cl.
*A61M 5/142*  (2006.01)
*A61M 5/158*  (2006.01)
*A61M 5/20*  (2006.01)

(52) U.S. Cl.
CPC ................. *A61M 5/14248* (2013.01); *A61M 2005/14256* (2013.01); *A61M 2005/1585* (2013.01);
(Continued)

(58) Field of Classification Search
CPC .... A61M 5/14248; A61M 2005/14256; A61M 2005/208; A61M 2205/103; A61M 2205/13; A61M 2005/1585
See application file for complete search history.

(56) References Cited

U.S. PATENT DOCUMENTS

2002/0055711 A1*  5/2002  Lavi .................... A61M 5/326
604/110
2008/0249473 A1* 10/2008  Rutti .................... A61M 5/158
604/157
(Continued)

FOREIGN PATENT DOCUMENTS

CN   101128228   2/2008
CN   101264354   9/2008
(Continued)

OTHER PUBLICATIONS

International Preliminary Report on Patentability in International Application No. PCT/EP2017/069135, dated Feb. 5, 2019, 9 pages.
(Continued)

*Primary Examiner* — Lauren P Farrar
(74) *Attorney, Agent, or Firm* — Fish & Richardson P.C.

(57) ABSTRACT

A medicament delivery device comprises a needle configured to move between a retracted position and an inserted position; an insertion mechanism to move the needle from the retracted position to the inserted position when activated; a locking arm which, in a locked position, is engaged with the insertion mechanism to prevent activation of the insertion mechanism and, in an unlocked position, is disengaged from the insertion mechanism; a retraction mechanism to move the needle from the inserted position to the retracted position when activated; and a trigger configured to move between a disengaged position and an engaged position. On moving from the disengaged position to the engaged position, the trigger is configured to move the locking arm from
(Continued)

the locked position to the unlocked position. On moving from the engaged position to the disengaged position, the trigger is configured to activate the retraction mechanism.

20 Claims, 10 Drawing Sheets

(52) U.S. Cl.
CPC . *A61M 2005/208* (2013.01); *A61M 2205/103* (2013.01); *A61M 2205/13* (2013.01)

(56) References Cited

U.S. PATENT DOCUMENTS

| | | |
|---|---|---|
| 2008/0319414 A1 | 12/2008 | Yodfat et al. |
| 2012/0078181 A1 | 3/2012 | Smith et al. |

FOREIGN PATENT DOCUMENTS

| | | |
|---|---|---|
| CN | 101784296 | 7/2010 |
| CN | 101909674 | 12/2010 |
| CN | 102470211 | 5/2012 |
| CN | 105251077 | 1/2016 |
| CN | 105492040 | 4/2016 |
| ES | 2365585 | 10/2011 |
| JP | 2004-501721 | 1/2004 |
| JP | 2008-220961 | 9/2008 |
| JP | 2013-510794 | 3/2013 |
| JP | 2013-517094 | 5/2013 |
| WO | WO 2001/017580 | 3/2001 |
| WO | WO 2002/002165 | 1/2002 |
| WO | WO 2004/098682 | 11/2004 |
| WO | WO 2009/062508 | 5/2009 |
| WO | WO 2011/012465 | 2/2011 |
| WO | WO 2011/060450 | 5/2011 |
| WO | WO 2011/090955 | 7/2011 |
| WO | WO 2015/032741 | 3/2015 |

OTHER PUBLICATIONS

International Search Report and Written Opinion in International Application No. PCT/EP2017/069135, dated Sep. 12, 2017, 12 pages.

* cited by examiner

MEDICAMENT DELIVERY DEVICE

CROSS REFERENCE TO RELATED APPLICATIONS

The present application is the national stage entry of International Patent Application No. PCT/EP2017/069135, filed on Jul. 28, 2017, and claims priority to Application No. EP 16182306.7, filed on Aug. 2, 2016, the disclosures of which are incorporated herein by reference.

TECHNICAL FIELD

The present invention relates to a device for delivery of medicament to a patient.

BACKGROUND

A variety of diseases exist that require regular treatment by injection of a medicament and such injections can be performed by using injection devices. Injection or infusion pumps of the type known as patch pumps for delivering injections of medicament are known in the art. Another type of injection pump that is gaining traction is the bolus injector device. Some bolus injector devices are intended to be used with relatively large volumes of medicament, typically at least 1 ml and may be a few ml. Injection of such large volumes of medicament can take some minutes or even hours. Such high capacity bolus injector devices can be called large volume devices (LVDs). Generally, such devices are operated by the patients themselves, although they may also be operated by medical personnel.

To use a patch pump or bolus injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

SUMMARY

According to an aspect a medicament delivery device is provided, including a needle configured to move between a retracted position and an inserted position; an insertion mechanism to move the needle from the retracted position to the inserted position when activated; a locking arm which, in a locked position, is engaged with the insertion mechanism to prevent activation of the insertion mechanism and, in an unlocked position, is disengaged from the insertion mechanism; a retraction mechanism to move the needle from the inserted position to the retracted position when activated; and a trigger configured to move between a disengaged position and an engaged position; wherein, on moving from the disengaged position to the engaged position, the trigger is configured to move the locking arm from the locked position to the unlocked position; and wherein, on moving from the engaged position to the disengaged position, the trigger is configured to activate the retraction mechanism.

The locking arm may be slideably mounted and pivotably coupled to an unlocking lever such that a rotation of the unlocking lever causes a sliding movement of the locking arm.

The trigger, on moving from the disengaged position to the engaged position, may engage with the unlocking lever to rotate the unlocking lever, such that the locking arm is moved from the locked position to the unlocked position.

The unlocking lever may be pivotably mounted at a midpoint, and may include a first end pivotably coupled to the locking arm and a second end arranged to engage with the trigger.

The unlocking lever may be formed having an angle at the pivot point, and may be arranged such that movement of the trigger along a first direction causes a rotation of the first end, and a resulting rotation of the second end causes a sliding movement of the locking arm along a second direction different to the first direction.

The insertion mechanism may include a user actuator arranged to be pushed by a user to activate the insertion mechanism.

The locking arm in the locked position may be engaged with the user actuator to prevent movement of the user actuator.

The locking arm may extend along the direction of sliding motion.

In the locking position, an end of the locking arm may be disposed within a receiving notch formed in the user actuator to prevent movement of the user actuator in a direction perpendicular to the locking arm.

In the unlocked position, the locking arm may be withdrawn from the notch.

The insertion mechanism may include biasing means to urge the needle towards the inserted position; and a blocking element arranged, in a blocking position, to prevent the needle from moving from the retracted position to the inserted position and arranged, in a release position, to allow the needle to move from the retracted position to the inserted position.

The user actuator may be arranged to urge the blocking element from the blocking position to the release position when pushed.

The insertion mechanism may include an injection arm pivotably mounted at one end and pivotably coupled to the needle at the other end; and a guide member configured to restrict movement of the needle to a linear movement between the retracted position and the inserted position in response to a pivoting action of the injection arm.

The blocking element in the blocking position may be arranged in abutment with the injection arm to prevent movement of the needle to the inserted position.

The blocking element may be pivotably mounted to rotate between the blocking position and the release position.

The blocking element may be formed having a substantially triangular shape which is pivotably mounted at a first corner.

A second corner of the blocking element may be in abutment with the injection arm when the blocking element is in the blocking position, and the user actuator may be configured to apply a force at a third corner of the blocking element when pushed.

The biasing means may include a torsion spring.

The torsion spring may be a coil spring fixed around the pivot of the injection arm.

A first end of the coil may be fixed in position, and a second end of the coil may extend along the injection arm to push the injection arm towards the inserted position.

The retraction mechanism may include a return actuator pivotably mounted to rotate between a first position and a second position.

The return actuator in the first position may be arranged to abut with the injection arm in the inserted position, and the return actuator may be configured to urge the injection arm and needle to the retracted position of the needle when moved to the second position.

The return actuator may be mounted to rotate around the pivot point of the injection arm.

The retraction mechanism may include biasing means configured to urge the return actuator towards the second position.

The trigger in the engaged state may be configured to engage with the return actuator to retain the return actuator in the first position, and the trigger in the disengaged state may be disengaged from the return actuator.

The biasing means may include a torsion spring.

The torsion spring may be a coil spring, having a first end of the coil fixed in position and a second end of the coil in abutment with the return actuator to push the return actuator towards the second position.

The coil of the torsion spring may not be fixed in position between the first end and second end.

The blocking element, in the blocking position, may be engaged with the return actuator to retain the return actuator in the first position and, in the release position, may be disengaged from the return actuator.

The trigger may be formed having a retaining slot.

In the first position, the return actuator may be aligned with the retaining slot, disposed within the retaining slot and prevented from moving to the second position when the trigger is in the engaged position, and may be released by the retaining slot when the trigger moves from the engaged position to the disengaged position.

The return actuator, in the second position, may be not aligned with the retaining slot and may abut with the trigger to prevent the trigger from moving from the disengaged position to the engaged position.

The trigger may be pivotably mounted to rotate between the engaged position and the disengaged position and the trigger may be biased towards the disengaged position.

The first end of the spring of the retraction mechanism may be fixed to the trigger to push the trigger towards the disengaged position.

The device may include an outer housing.

In the retracted position, the needle may be disposed within the housing and, in the inserted position, the needle may extend out of the housing.

The needle in the inserted position may extend through a contact surface of the housing, and the trigger in the disengaged position may extend through the contact surface.

The trigger in the disengaged position may extend beyond the needle in the inserted position.

The trigger in the engaged position may be disposed within the housing, and the trigger may be configured to be moved to the engaged position when the contact surface is placed against a user.

The trigger may be pivotably mounted to a point within the housing, such that the trigger extends parallel to the contact surface in the engaged position, and extends at an angle from the contact surface in the disengaged position.

A vertical extent of the housing, measured perpendicular to the contact surface, may be smaller than a horizontal extent of the housing.

The device may include a medicament reservoir and a medicament which is retained in the medicament reservoir.

These and other aspects of the invention will be apparent from and elucidated with reference to the embodiments described hereinafter.

BRIEF DESCRIPTION OF THE FIGURES

Exemplary embodiments of the present invention are described with reference to the accompanying drawings, in which.

DETAILED DESCRIPTION

Figure 1:
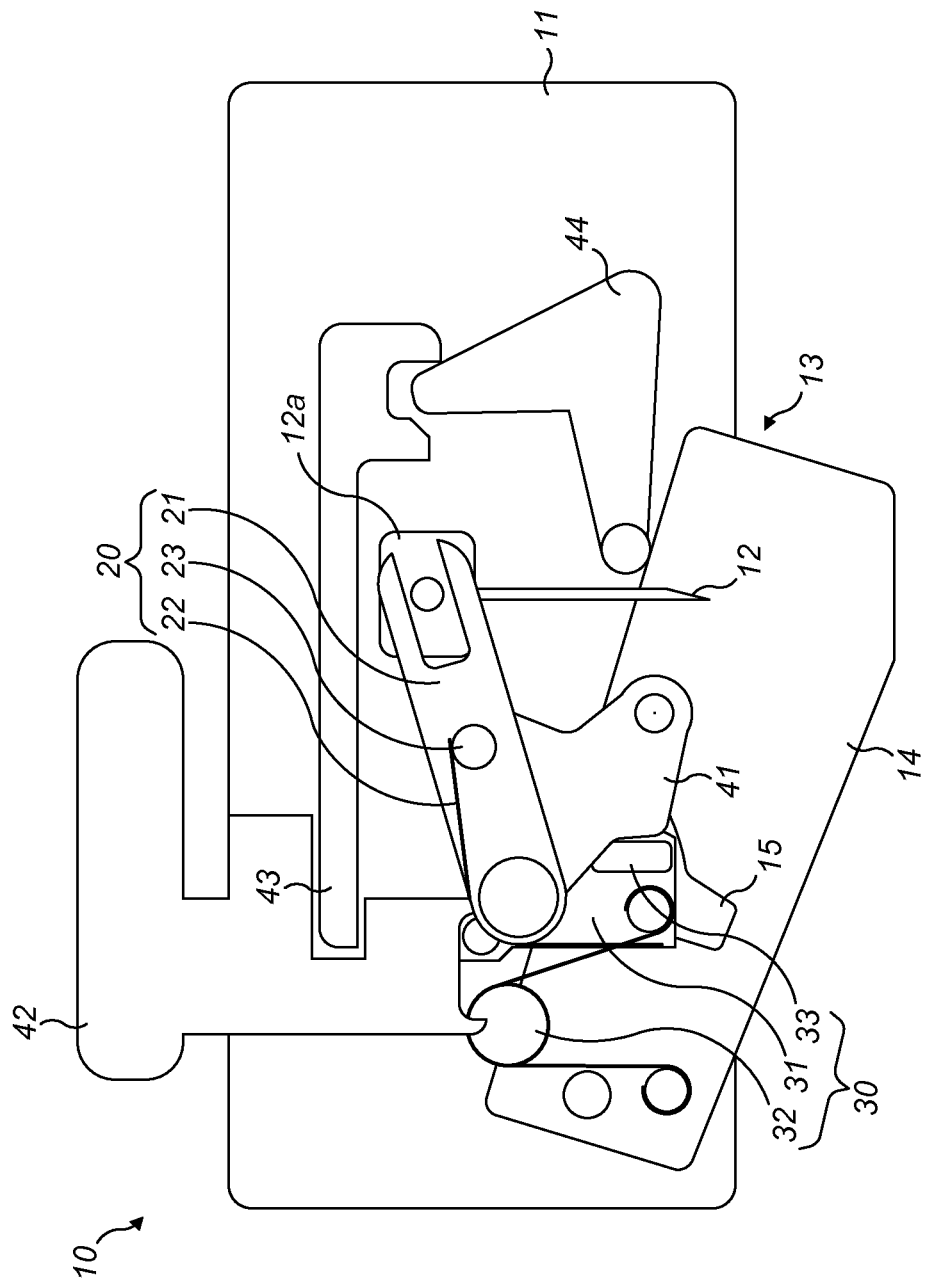
FIG. 1 is a schematic side view of an injection device according to an embodiment.

A medicament delivery device, as described herein, may be configured to inject a medicament into a patient. For example, delivery could be sub-cutaneous, intra-muscular, or intravenous. Such a device could be operated by a patient or by a care-giver, such as a nurse or physician. The device can include a cartridge-based system that requires piercing a sealed ampule before use.

The device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g. about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The medicament delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of a device may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a trigger against their body in order to cause injection of a medicament. Other devices may require a multi-step activation of an automated function. For example, a user may be required to depress a button and deploy a needle in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some medicament delivery devices can also include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 2:
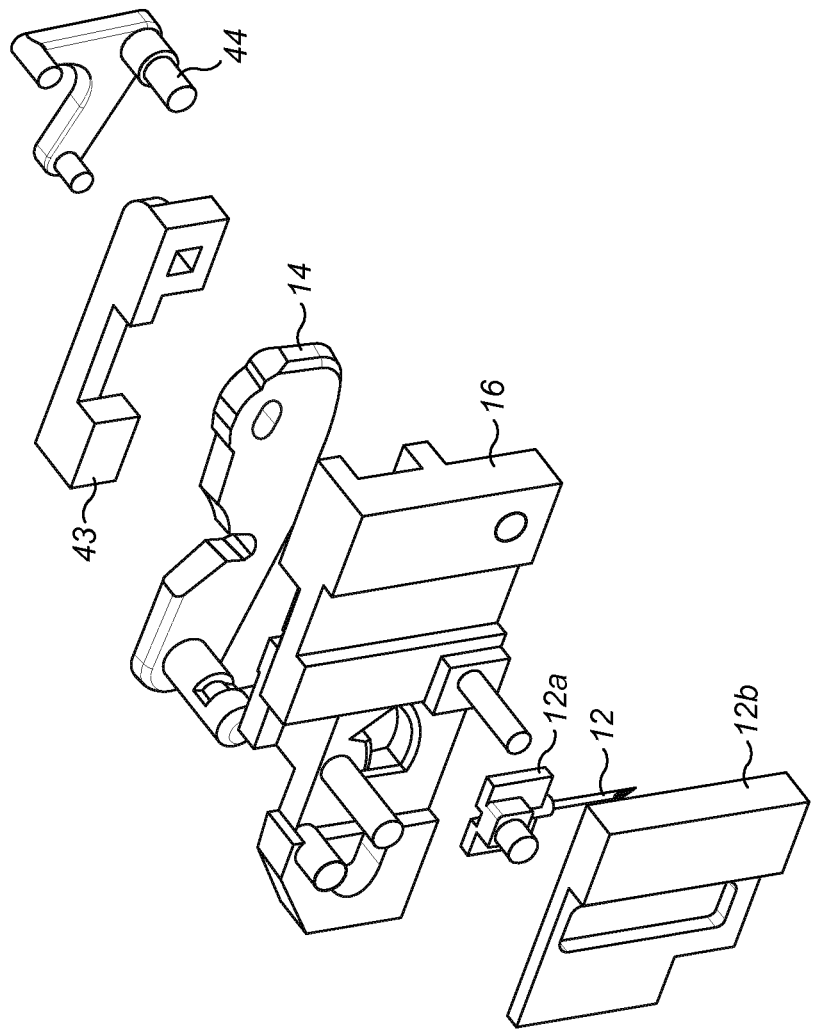
FIG. 2 is an exploded view of the FIG. 1 injection device.

FIGS. 1 and 2 show a medicament delivery device 10, which in the exemplary embodiment comprises a bolus injector device (hereafter simply referred to as "device 10"), according to a first embodiment. The device 10 comprises a housing 11 containing a medicament delivery mechanism. The device 10 can include an LVD.

FIG. 1 is a schematic cross-section view showing the device 10. FIG. 2 is an exploded view showing components of the medicament delivery system. The medicament delivery mechanism is only shown schematically and a number of the functional components are omitted for the sake of clarity and brevity, but the device 10 includes a needle 12 for injection of the liquid medicament into a patient's body. The liquid medicament may be provided in a reservoir (not shown) within the medicament delivery mechanism, or may be provided externally of the device 10.

Although not shown in the figures, a medicament delivery mechanism of a device may include one or more of the following components. A controller configured to control operation of the device 10. A medicament reservoir containing a supply of medicament to be administered to a patient. The medicament reservoir may, for example, include a cartridge or a vial formed of glass. A plunger may be provided within the cartridge and plunger driver mechanically coupled to the plunger. The plunger driver may be controllable to move the plunger along the medicament cartridge. The force provided by the plunger causes medicament to be expelled through a medicament delivery aperture in the medicament cartridge and along a medicament delivery tube to the needle 12 to be expelled through the bore of the needle 12. An electrical power source in the form of a battery to power to the controller. The battery may also provide electrical power the plunger driver, if this is an electrically driven device.

The housing 11 is shown schematically as a rectangular case in FIG. 1. The housing 11 may be a box having a rectangular cross section. Alternatively, the housing 11 may be cylindrical, with the cross section shown through the widest point. Further alternatively, the housing 11 may be approximately dome shaped or may have any other suitable shape and profile to contain the components of the medicament delivery mechanism.

The housing 11 includes a support 16, as shown in FIG. 2. The support 16 is fixed in position with the housing 11. The support 16 fixes the positions and movements of the components of the medicament delivery mechanism, as will be described below.

The device 10 generally comprises a housing upper side 11a and a lower side 11b. The lower side 11b is flat. The upper side 11a may be flat and parallel to the lower side 11b. Alternatively, the upper side 11a may be curved or shaped e.g. to be easily held. In an alternative embodiment to lower side 11b may be curved. The lower side 11b may be shaped to fit against the patient's skin when the device 10 is in position.

In use, the lower side 11b of the housing 11 is intended to be a contact surface that is placed against a patient's skin during a medicament administration process. The lower side 11b forms a flat contact surface. The lower side 11b may comprise an adhesive layer to removably adhere to a patient's skin. The lower side 11b may include a cushioning layer, for example, a foam or gel layer. A height of the device 10, measured between the upper side 11a and the lower side 11b, may be short with respect to the size of the lower side 11b. A length of the lower side 11b may be greater than the height of the device 10. A width of the lower side 11b may be greater than the height of the device 10. The device 10 is stable when placed in position against a patient's skin.

The contact surface or lower side 11b of the housing 11 includes an aperture 13 through which the needle 12 can project in use. The needle 12 is arranged to extend in a direction perpendicular to the lower side 11b. A length of needle 12 defines a first axis of the device 10. The first axis is perpendicular to the contact surface with a patient's skin when the lower side 11b is placed against the patient's skin. The height of the device 10 is measured along the first axis.

A second axis of the device 10 is perpendicular to the first axis. The second axis is parallel to the lower side 11b of the housing 11. FIG. 2 shows an exploded view of the device 10, with components of the medicament delivery system separated along the second axis. In FIG. 1, the second axis extends perpendicular to the plane of the cross section. A third axis of the device 10 is perpendicular to the first axis and the second axis. In FIG. 1, the third axis extends horizontally from left to right.

The needle 12 of the device 10 is moveable along the first axis. The needle 12 is prevented from moving except to move along its length. The needle 12 can be moved between a retracted position and an inserted position. In the retracted position the needle 12 is disposed within the housing 11 of the device 10. In the inserted position, the needle 12 projects from the lower side 11b of the housing 11 through the aperture 13. The needle 12 is arranged in the inserted position so as to pierce and inject a patient's skin when the device 10 is attached to a patient.

The needle 12 is fixedly attached to a needle support 12a. The needle 12 is attached at an upper end to the needle support 12a. The needle 12 extends downwards from the needle support 12a. The needle support 12a is a thin rectangular plate. The needle support 12a is arranged in a plane perpendicular to the second axis. The needle support 12a may be any other suitable shape.

The needle 12 and needle support 12a are arranged to fit within a corresponding groove in the housing support 16. The groove in the housing support 16 extends vertically along the first axis. The needle support 12a is in abutment with the sides of the groove. The needle 12 is prevented from moving sideways along the third axis when the needle support 12a is disposed in the groove.

The needle support 12a comprises a lateral protrusion. The needle support 12a has a protrusion extending along the second axis. The protrusion of the needle support 12a extends away from the housing support 16. The protrusion extends out of the groove of the housing support 16. The protruding part of the needle support 12a is arranged to engage with a needle guide 12b.

The needle guide 12b is a generally rectangular frame. The needle guide 12b is arranged in a plane perpendicular to the second axis. The needle guide 12b comprises a vertical slot extending along first axis. The protruding part of the needle support 12a extends into the slot of the needle guide 12b. The needle support 12a is in abutment with the sides of the slot of the needle guide 12b. The needle guide 12b prevents the needle 12 and the needle support 12a from sideways movement along the third axis.

The needle guide 12b is fixed in position against the housing support 16. The needle support 12a and the needle 12 are arranged between the housing support 16 and the needle guide 12b. The needle guide 12b retains the needle support 12a in the groove of the housing support 16. The needle guide 12b prevents the needle 12 and needle support 12a from movement along the second axis. The needle 12 is therefore free to move along the first axis only The medicament delivery mechanism of the device 10 comprises a needle insertion mechanism 20, a needle retraction mechanism 30 and a trigger arrangement 40. The needle insertion mechanism 20 is configured to move the needle 12 from the retracted position into the inserted position. The needle retract mechanism 30 is configured to retract the needle 12 from the inserted position into the retracted position. The trigger arrangement 40 allows the user to activate the medicament delivery process. The trigger arrangement 40 may activate the needle insertion mechanism 20. Elements of the trigger arrangement 40 may be considered to be part of the needle insertion mechanism 20.

The device 10 further comprises a contact trigger 14. The contact trigger 14 is an example of a trigger. The contact trigger 14 is configured to control the operation of the insertion mechanism 20 and the retraction mechanism 30 according to whether or not the device 10 is placed on the body of a patient. Alternatively, the device may include a manual trigger. For example, the trigger may be a grip trigger, to ensure the device is held securely throughout the medicament delivery process.

The contact trigger 14 is configured to lock the insertion mechanism 20 until the device 10 is placed on a contact surface. The contact trigger 14 can prevent activation of the insertion mechanism 20 when the device 10 is not placed on the body. The contact trigger 14 is further configured to activate the retraction mechanism 30 when the device 10 is removed from the body. The contact trigger 14 of the device 10 can prevent unintentional activation of the insertion mechanism 20 when the device 10 is not in position on the body of a patient. The contact trigger 14 also avoids unnecessary exposure of the needle 12 when the medicament delivery process has been completed. The contact trigger 14 can improve the safety of the medicament delivery operation.

The needle insertion mechanism 20 comprises an injection arm 21 and an injection spring 22. The injection arm 21 is an elongate member. The injection arm 21 is configured to pivot around a point at one end of the injection arm 21. The injection arm 21 is fixed to the housing support 16 at the pivot point. The injection arm 21 comprises a circular hole at the pivot point, configured to fit over a corresponding axle extending from the housing support 16. The injection arm 21 freely rotates around the axle of the housing support 16. The injection arm 21 is arranged to rotate in a plane perpendicular to the second axis.

The needle 12 is coupled to the end of the injection arm 21 distal from the pivot. The injection arm 21 comprises an elongate slot extending along the injection arm 21. The slot of the injection arm 21 may be open at the distal end of the injection arm 21, as shown in FIG. 1. Alternatively, the slot of the injection arm 21 may be closed at end, as shown in FIG. 2.

The injection arm 21 is configured to engage with the needle support 12a. The protruding part of the needle support 12a passes through the slot of the injection arm 21. The needle guide 12b is disposed between the injection arm 21 and the needle 12. The injection arm 21 extends generally along the third axis, such that rotation about the pivot causes the distal end to move up and down along the first axis. As the injection arm 21 is rotated, the sides of the slot exert a force on the needle support 12a. The injection arm 21 exerts a force on the needle support 12a in an upwards or downwards direction along the first axis.

Figure 3A:
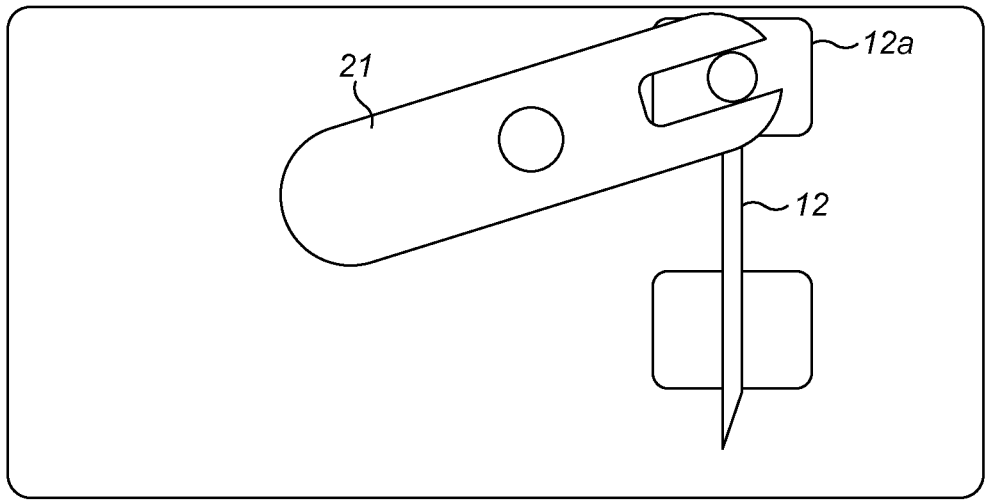
FIG. 3A is a schematic side view of the FIG. 1 injection device.
Figure 3B:
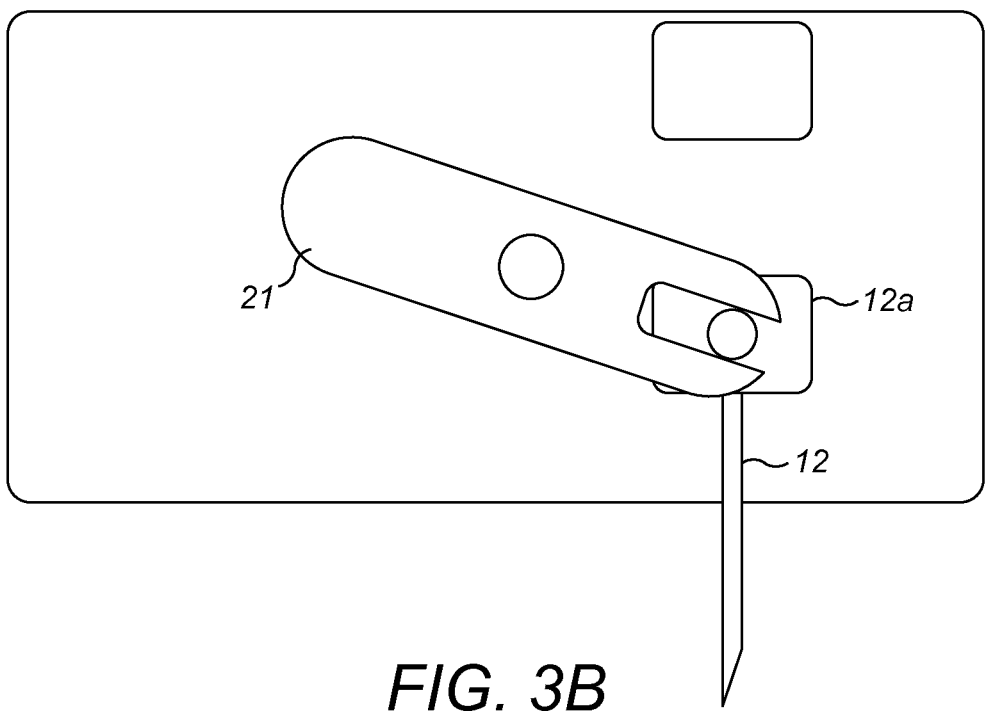
FIG. 3B is a schematic side view of the FIG. 1 injection device.

Rotation of the injection arm 21 causes the needle support 12a to move along the groove of the housing support 16. Rotation of the injection arm 21 is translated into movement of the needle 12 along the first axis. The injection arm 21 is configured to pivot between a retracted position and an inserted position, corresponding to the retracted position and the inserted position of the needle 12. The retracted position of the injection arm 21 is shown in FIG. 3A and the inserted position is shown in FIG. 3B.

The injection arm 21 comprises a peg 23. The peg 23 is arranged to engage with the injection spring 22. The peg 23 is also for engaging with the trigger arrangement 40. The peg 23 is positioned midway along injection arm 21. The peg 23 may be positioned at any point between the pivot and the slot of the injection arm 21. The peg 23 extends from the injection arm 21 along the second axis. The peg 23 extends in a direction away from the housing support 16.

The injection spring 22 is an example of a needle driver to drive the needle insertion mechanism 20. The injection spring 22 is a torsion spring, for example, a wire coil spring with a straight portion extending from each end of the coil. The ends of the injection spring 22 extend with an angle between them. The injection spring 22 is tensioned so as to reduce the angle between the ends of the coil when released. Alternatively, the needle driver may be, for example, a linear coil spring, a hydraulic or pneumatic piston, or an electric motor. A battery may provide an energy source to power the needle driver. The injection spring 22 is configured to move the needle 12 from the retracted position to the inserted position.

The injection spring 22 is arranged to apply a force which moves the injection arm 21 to the inserted position. The coil of the injection spring 22 is disposed around the pivot point of the injection arm 21. The coil is disposed around the same axle of the housing support 16 as the injection arm 21. A first end of the injection spring 22 is fixed in position. A further peg protruding from the housing support 16 is arranged in abutment with the first end of the injection spring 22. The housing support 16 prevents the first end of the injection spring 22 from moving towards a second end of the injection spring 22.

The second end of the injection spring 22 is arranged in abutment with the peg 23 of the injection arm 21. The second end of the injection spring 22 is placed on top of the peg 23. The peg 23 is positioned between the two ends of the injection spring 22. The peg 23 prevents the second end of the injection spring 22 from moving towards the first end. The injection spring 22 exerts a downwards force on the peg 23.

Figure 4A:
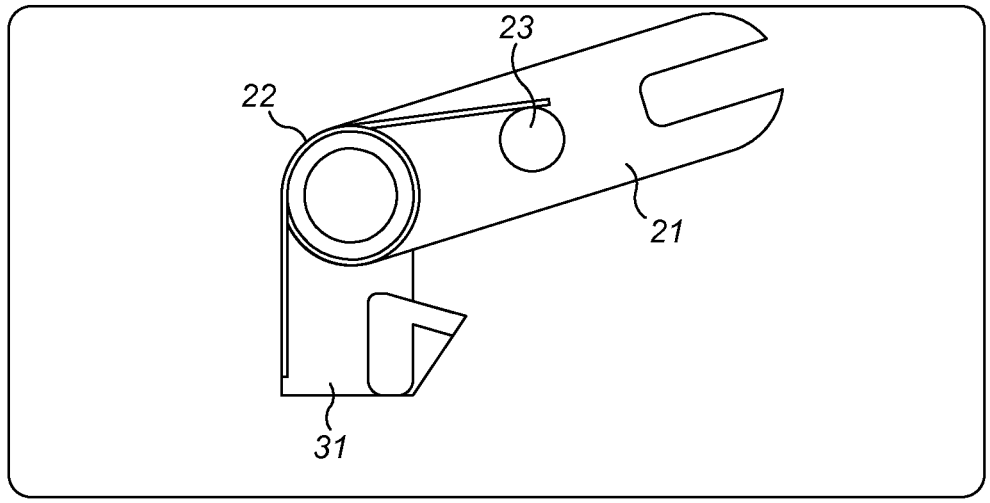
FIG. 4A is a schematic side view of the FIG. 1 injection device.
Figure 4B:
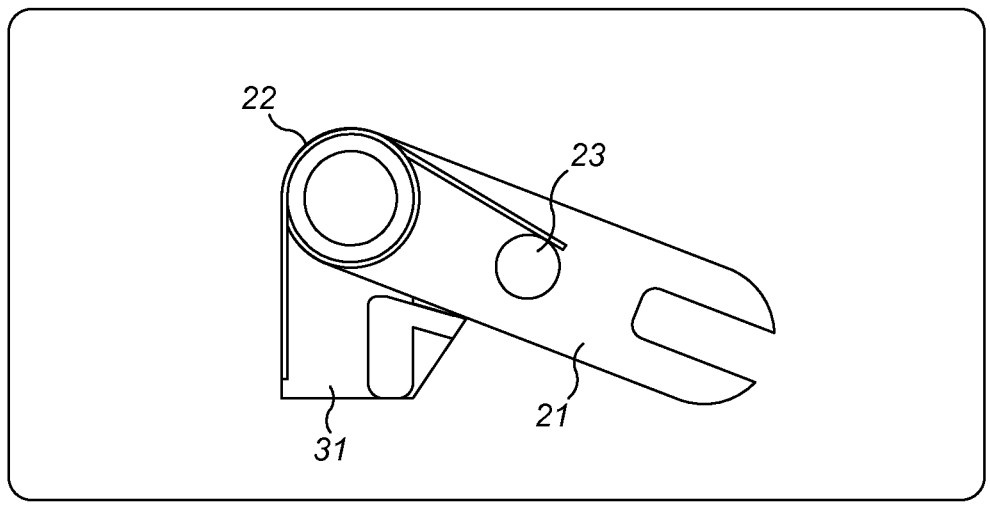
FIG. 4B is a schematic side view of the FIG. 1 injection device.

The injection spring 22 can cause a rotation of the injection arm 21, as shown in FIGS. 4A and 4B. When the injection arm 21 is in the retracted position, as shown in FIG. 4A, the injection spring 22 exerts a downwards force on the peg 23 of the injection arm 21 along the first axis. The injection spring 22 can cause the injection arm 21 to rotate to the inserted position, as shown in FIG. 4B.

The trigger arrangement 40 comprises a blocking element 41 and a button 42. The blocking element 41 is coupled between the button 42 and the injection arm 22. The blocking element 41 comprises a thin, generally triangular element. The blocking element 41 is arranged in a plane perpendicular to the second axis. A first corner of the blocking element 41 forms a pivot point of the blocking element 41. The blocking element 41 is configured to rotate around the first corner. The blocking element 41 is fixed to the housing support 16 at the pivot point. The blocking element 41 comprises a circular hole positioned at the first corner, configured to fit over a corresponding axle extending from the housing support 16. The blocking element 41 freely rotates around the axle of the housing support 16. The blocking element 41 is arranged to rotate in a plane perpendicular to the second axis.

A second corner of the blocking element 41 is configured to engage with the injection arm 21. The blocking element 41 is configured to engage with the peg 23 of the injection arm 21. The second corner of the blocking element 41 comprise a cut away portion forming a notch. The pivot point of the blocking element 41 is positioned below the peg 23. The distance between the first corner and the second corner of the blocking element 41 is configured to equal the distance between the pivot point of the blocking element 41 and the peg 23.

Figure 5A:
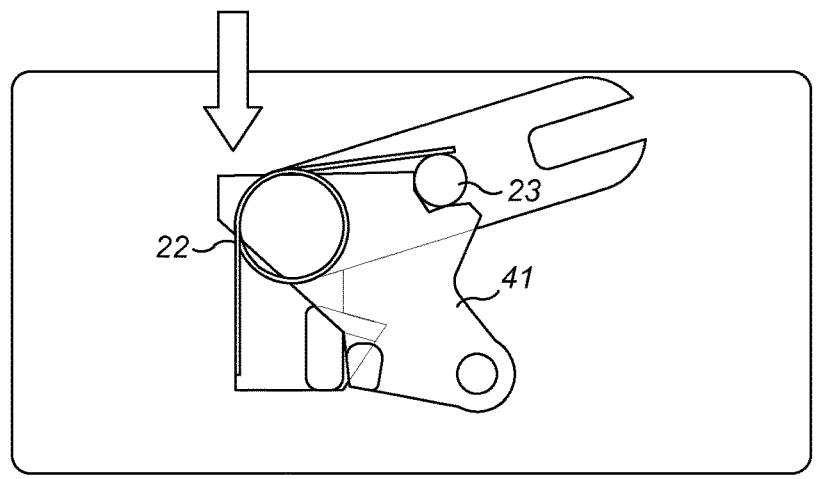
FIG. 5A is a schematic side view of the FIG. 1 injection device.
Figure 5B:
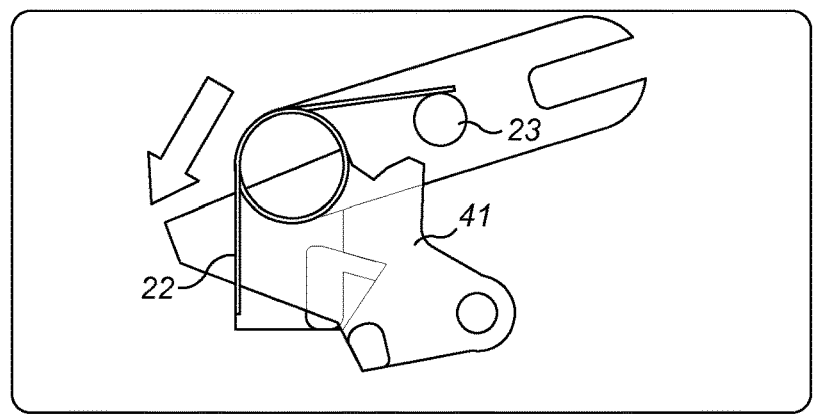
FIG. 5B is a schematic side view of the FIG. 1 injection device.
Figure 5C:
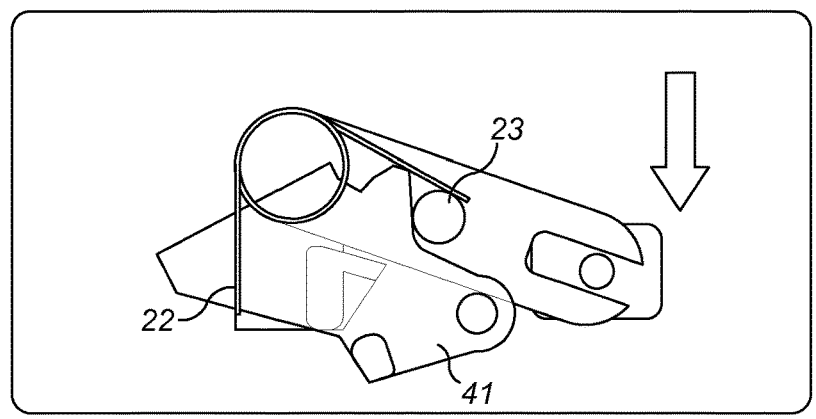
FIG. 5C is a schematic side view of the FIG. 1 injection device.

The blocking element 41 is configured to rotate between a blocking position and a release position, as shown in FIGS. 5A, 5B and 5C.

In the blocking position, as shown in FIG. 5A, the blocking element 41 is arranged to prevent the injection arm 21 from moving to the inserted position. The blocking element 41 is rotated such that the second corner is above the pivot point. The blocking element 41 engages with the peg 23 to prevent movement of the injection arm 21. The peg 23 is located in the notch at the second corner of the blocking element 41. The blocking element 41 prevents the needle 12 from moving to the inserted position in the blocking position.

In the release position, as shown in FIG. 5B, the blocking element 41 is rotated with respect to the blocking position. The peg 23 is not restrained by the second corner of the blocking element 41 in the release position. The blocking element 41 allows the injection arm 21 to rotate under the influence of the injection spring 22. The release position of the blocking element 41 allows the injection arm to move to the inserted position, as shown in FIG. 5C. A side of the blocking element 41 between the first corner and the second corner may be recessed to allow the movement of the peg 23.

A third corner of the blocking element 41 is configured to be level with the second corner in the blocking position. The blocking element 41 comprises an engaging peg disposed at the third corner. The engaging peg of the blocking element 41 protrudes from the triangular element along the second axis. The engaging peg is arranged to engage with the button 42.

The button 42 is arranged to be pushed by, for example, a patient or care-giver. The button 42 extends out of the housing 11. The button 42 extends though the upper side 11a of the housing 11. The button 42 is formed with an enlarged upper end. The button 42 may be formed with any shape to be pushed by the user. The button 42 may include a lever arrangement.

The button 42 is configured to move freely along the first axis. A lower portion of the button 42 is in abutment with the engaging peg of the blocking element 41. A downwards force on the button 42 exerts a corresponding downwards force on the blocking element 41. A force applied to the upper end of the button 42 therefore causes the blocking element 41 to rotate. The blocking element 41 is moved from a blocking position to a release position when the button 42 is pushed.

The trigger arrangement 40 further comprises a button latch comprising, for example, a locking arm 43 and an unlocking lever 44. The locking arm 43 is an elongate member. The locking arm 43 is arranged horizontally within the housing 11. The locking arm 43 extends along the third axis of the device 10. The locking arm 43 is restrict to move along the third axis only. The locking arm 43 is retained in a horizontal groove formed in the housing support 16. The upper and lower sides of the locking arm 43 are in abutment with the sides of the groove formed in the housing support 16. The groove restricts the locking arm 43 from movement along the first axis.

The locking arm 43 is arranged to engage with the button 42 at one end. The button 42 is formed having a receiving notch on one side. An end portion of the locking arm 43 is configured to fit within the receiving notch of the button 42. When the locking arm 43 is in position in the notch of button 42, the upper surface of the locking arm 43 is in abutment with the upper side of the receiving notch. The locking arm 43 is restricted from movement along the first axis and can restrict the button 42 from movement along the first axis.

The unlocking lever 44 is a V-shaped element. The unlocking lever 44 is arranged to pivot about a midpoint of the unlocking lever 44. A first end and a second end of the unlocking lever 44 extend away from the pivot point. An acute angle is formed between the two ends of the unlocking lever 44. Alternatively, the unlocking lever 44 may be formed having a right angle, or an obtuse angle between the two ends. Further alternatively, the two ends of the unlocking lever 44 may be formed to have different lengths. The unlocking lever 44 is fixed to the housing support 16 at the pivot point. The unlocking lever 44 comprises a circular protrusion configured to fit within a corresponding hole formed in the housing support 16. The unlocking lever 44 freely rotates in a plane perpendicular to the second axis.

The unlocking lever 44 is coupled to the locking arm 43 at the first end. The first end of the unlocking lever 44 comprises a circular peg extending in the direction of the second axis. The circular peg is configured to fit within a corresponding hole formed in the locking arm 43. The unlocking lever 44 engages with the locking arm 43 at an end furthest from the button 42. Alternatively, the peg formed at the first end of the unlocking lever 44 may engage with a notch formed in a lower surface of the locking arm 43, as shown in FIG. 1. Further alternatively, the first end of the unlocking lever 44 may be engaged directly with the notch in the locking arm 43.

The point of engagement between the first end of the unlocking lever 44 and the locking arm 43 is generally above the pivot point of the unlocking lever 44. Rotation of the unlocking lever 44 results in a movement of the first end of the unlocking lever 44 along the third axis. The unlocking lever 44 engages with the notch formed in the locking arm 43 when rotated to exert a force on the locking arm 43 along the third axis.

A pivoting movement of the unlocking lever 44 causes a sliding movement of the locking arm 43. The locking arm 43 and unlocking lever 44 are configured to move between a locked position and an unlocked position. In the locked position, the unlocking lever 44 is engaged with the button 42. The unlocking lever 44 prevents the button 42 from being pushed in the locked position. In the unlocked position, the unlocking lever 44 is disengaged from the button 42. The unlocking lever 44 is arranged to engage with the contact trigger 14 at the second end.

The contact trigger 14 is formed as a rectangular arm. The contact trigger 14 extends generally along the third axis of the device 10. The contact trigger 14 is formed to be relatively thin in the direction of the second axis. The contact trigger 14 is configured to pivot about a point at one end of the rectangular arm. The contact trigger 14 is fixed to the housing support 16 at the pivot point. The contact trigger 14 is formed having a circular peg which is arranged to fit within a corresponding circular hole formed in the housing support 16. The contact trigger 14 is configured to freely rotate in the circular hole in a plane perpendicular to the second axis.

Figure 6A:
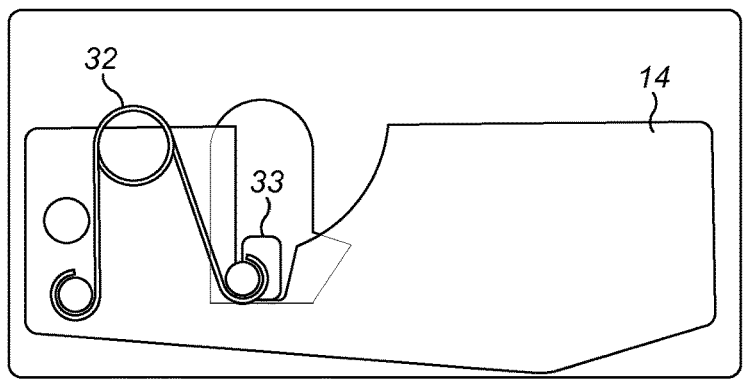
FIG. 6A is a schematic side view of the FIG. 1 injection device.
Figure 6B:
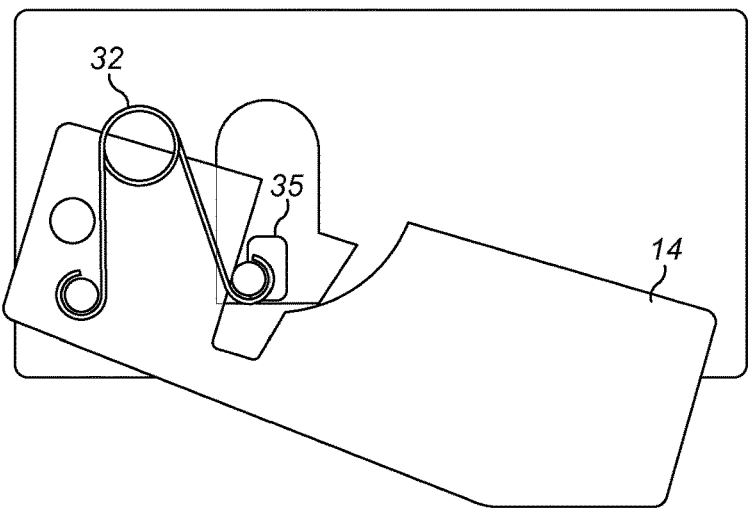
FIG. 6B is a schematic side view of the FIG. 1 injection device.
Figure 6C:
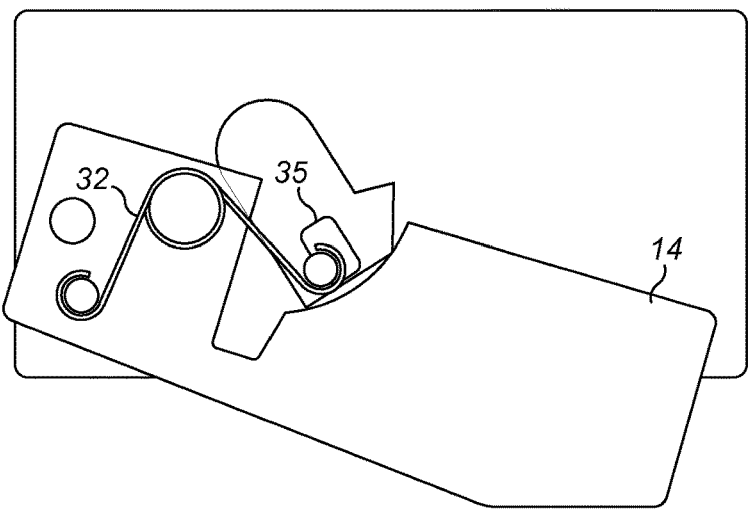
FIG. 6C is a schematic side view of the FIG. 1 injection device.

The contact trigger 14 is moveable between a disengaged position and an engaged position, as shown in FIGS. 6A, 6B and 6C. In the engaged position the contact trigger 14 is disposed entirely within the housing 11. The contact trigger 14 extends horizontally from the pivot point, along the third axis. The contact trigger 14 lies parallel to the lower side 11b. The lower edge of the contact trigger 14 is above the lower side 11b of the housing 11.

In the disengaged position, the contact trigger extends from the lower side 11b of the housing 11. The contact trigger 14 is rotated with respect to the engaged position. The contact trigger 14 is angled down from pivot point. The contact trigger 14 extends through a corresponding slot formed in the lower side 11b. The contact trigger 14 is biased towards the disengaged position. The end of the contact trigger 14 which is furthest from the pivot point forms the lowest point of the contact trigger 14 in the disengaged position. The lowest corner of the contact trigger 14 in the disengaged position may be truncated. The lowest corner may be formed as an edge which is parallel to the lower side 11b in the disengaged position.

An upper side of the contact trigger 14 is in contact with the unlocking lever 44. FIG. 6A shows the contact trigger in an initial state, in the disengaged position. The second end of the unlocking lever 44 comprises a protruding part. The protruding part extends from the unlocking lever 44 along the second axis. The protruding part of the locking arm rests on an upper side of the contact trigger 14. Alternatively, the protruding part passes through a corresponding hole formed in the contact trigger 14, as shown in FIG. 2. Further alternatively, the contact trigger 14 may engage directly with a lower surface of the second end of the unlocking lever 44.

A force applied upwards along the first axis to the contact trigger 14 exerts a corresponding upwards force on the unlocking lever 44. The second end of the unlocking lever 44, which is engaged with the contact trigger 14, is positioned to the side of the pivot point of the unlocking lever 44. As the second end of the unlocking lever 44 moves upwards along the first axis, the unlocking lever 44 rotates around the pivot point. The rotation moves the first end of the unlocking lever 44 along the third axis, causing a sliding movement of the locking arm 43 as described above.

FIG. 6B shows the contact trigger 14 in the engaged position. Movement of the contact trigger 14 from the disengaged position to the engaged position causes rotation of the unlocking lever 44 and moves the locking arm horizontally, as described. The button 42 can be moved along the first axis when the contact trigger 14 is in the engaged position. The button 42 can be pressed to rotate the blocking element 41 as described above, as shown in FIG. 6C.

The needle retraction mechanism 30 comprises a return actuator 31 and a return spring 32.

The return actuator 31 comprises an engaging part 33 for engaging with the blocking element 41, a peg 34 for engaging with the return spring 32 and a locking part 35 for engaging with the contact trigger 14. The elements of the return actuator 31 are formed in a single piece. The return actuator 31 is arranged to rotate in a plane perpendicular to the second axis. The return actuator 31 is fixed to the housing support 16 at a pivot point. The return actuator 31 is formed having a circular hole which fits over a corresponding axle extending from the housing support 16. The return actuator 31 is configured to rotate freely around the axle of the housing support 16. The return actuator 31 is arranged on the same axle as the injection arm 21 and the injection spring 22. According to the embodiment, the return actuator 31 is mounted between the injection arm 21 and the housing support 16.

The engaging part 33 protrudes along second axis from the return actuator 31. The engaging part 33 extends the in direction of the injection arm 21. The engaging part 33 is positioned below the injection arm 31. The engaging part 33 comprises a flat surface for engaging with the lower side of the injection arm 21.

The peg 34 extends along second axis from the return actuator 31. The peg 34 extends from the opposite side of the return actuator 31 to the engaging part 33. The return actuator 31 is arranged between to the injection arm 21 and the return spring 32. The peg 34 is arranged to engage with the return spring 32.

The return spring 32 is an example of a retraction driver to drive the retraction mechanism 30. The return spring 32 is a torsion spring, for example, a wire coil spring with a straight portion extending from each end of the coil. The ends of the return spring 32 extend with an angle between them. The return spring 32 is tensioned so as to increase the angle between the ends of the coil when released. Alternatively, the retraction driver may be, for example, a linear coil spring, a hydraulic or pneumatic piston, or an electric motor. A single electric motor may be used to drive the insertion mechanism 20 and the retraction mechanism 30.

The coil of the return spring 32 is fixed in position with respect to the housing support 16. The coil is arranged around a peg which extends from the housing support 16 along the second axis. A first end of the return spring 32 is fixed in position. The first end is fixedly attached to the contact trigger 14, as will be described below. Alternatively, the first end of the return spring 32 may be fixed to an element of the housing 11 or support 16. The first end of the return spring 32 is prevented from moving away from a second end of the return spring 32. The second end of the return spring 32 is coupled to the peg 34 of the return actuator 31. The second end of the return spring 32 is formed in a loop which wraps around the peg 34. The return spring 32 exerts a force pushing against the peg 34.

Figure 7A:
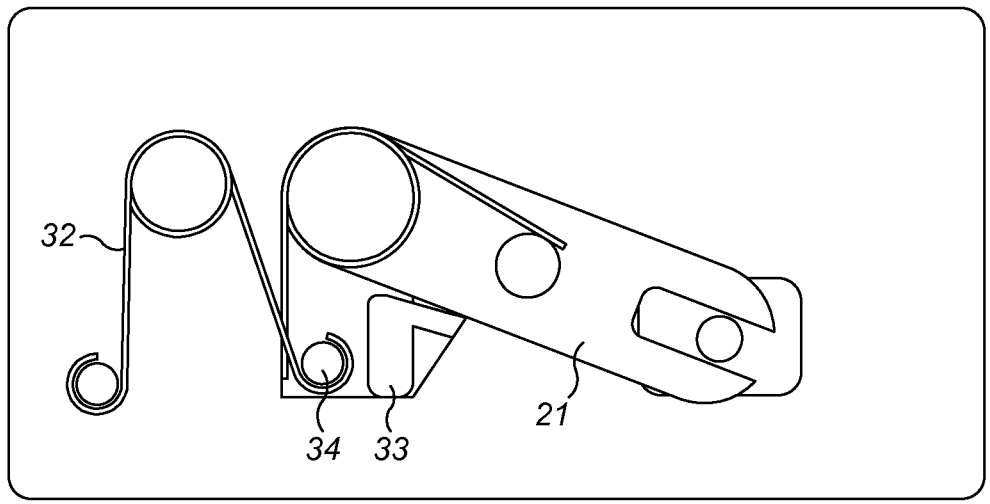
FIG. 7A is a schematic side view of the FIG. 1 injection device.
Figure 7B:
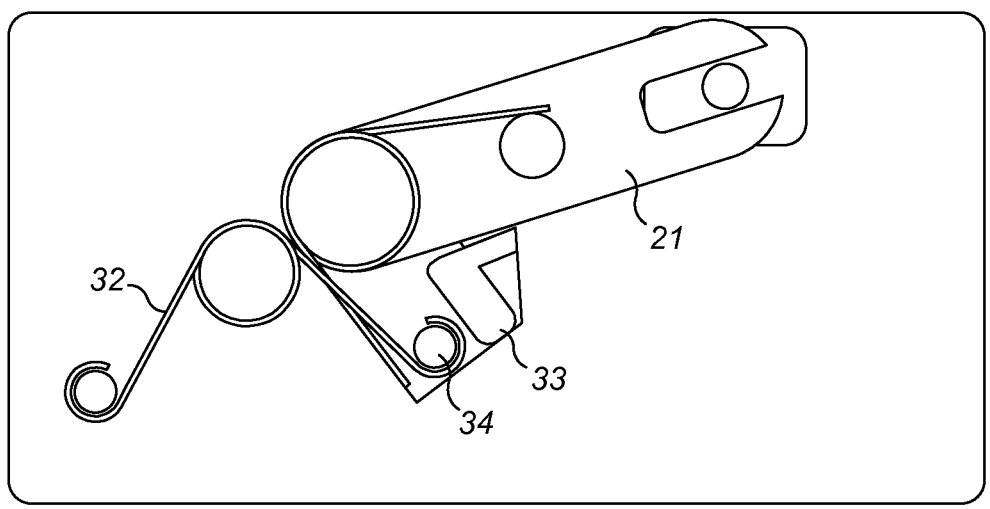
FIG. 7B is a schematic side view of the FIG. 1 injection device.

The return spring 32 is configured to move the needle 12 from the inserted position to the retracted position, as shown in FIGS. 7A and 7B. The return actuator 31 is configured to move between a first position and a second position, in response to a force from the return spring 32. In the first position, as shown in FIG. 7A, the return actuator 31 is positioned below the pivot point. The engaging part 33 is in the lowest position along the first axis. When the injection arm 21 is in the inserted position, the lower side of the injection arm 21 is in abutment with the engaging part 33.

The return spring 32 is arranged to apply a force which moves the return actuator 31 to the second position. The first end of the return spring 32 is positioned to the side of the return actuator 32, along the third axis. The tension of the return spring 32 pushes the two ends apart. The return spring 32 exerts a force on the peg 34 along the third axis. The return actuator 32 rotates to the second position in response to the force from the return spring 32. The return spring 32 pushes the return actuator 32 against the injection arm 21.

The second position of the return actuator 31 is shown in FIG. 7B. Rotation of the return actuator 32 moves the engaging part 33 along the third axis and upwards along the first axis. The engaging part 33 exerts a corresponding force on the injection arm 21 upwards along the first axis. The injection arm 21 rotates in response to the force from the engaging part 33. The injection arm 21 is rotated from the inserted position to the retracted position by the movement of the return actuator 31.

The force exerted by the return spring 32 is larger than the force exerted by the injection spring 22. The injection arm 21 and the needle 12 will rest in the retracted position when both springs act on the injection arm 21. Alternatively, the injection arm 21 may be disengaged from the injection spring 22 when moved from the retracted position to the inserted position.

The engaging part 33 of the return actuator 31 is further configured to engage with the blocking element 41. The engaging part 33 extends downwards from the surface which engages the injection arm 21. When the return actuator 31 is in the first position, the engaging part 33 extends along the first axis. The engaging part 33 provides a vertically extending surface to engage with the blocking element 41. The engaging part 33 is arranged to engage a blocking part 41a of the blocking element 41.

The blocking part 41a comprises a rectangular protrusion extending along the second axis from the blocking element 41. The blocking part 41a is positioned part way between the first corner and the third corner of the blocking element 41. The interaction between the engaging part 33 and the blocking part 41a can be seen in FIGS. 5A and 5B.

When the blocking element 41 is in the blocking position, and the return actuator 31 is in the first position, the engaging part 33 is engaged with the blocking part 41a. FIG. 5A shows the blocking part 41a in abutment with the engaging part 33. The engaging part 33 and the blocking part 41a are in contact along a vertical surface. The blocking part 41a cannot move along the third axis due to the fixed pivot point of the blocking element 41. The engaging part 33 is restrained from moving along the third axis in the direction of the blocking part 33. The blocking part 33a is arranged on the side of the engaging part 33 away from the return spring 32. The engaging part 33 is pushed against the blocking part 41a by the return spring 32. The return actuator 31 is prevented from moving to the second position by the blocking part 41a.

When the blocking element 41 is rotated to the release position, as shown in FIG. 5B, the blocking part 41a moves down along the first axis. The blocking part 41a is moved below the extent of the engaging part 33. The blocking part 41a is not in contact with the engaging part 33 in the release position. The engaging part 33 can move past the blocking part 41a and the return actuator 31 can move to the second position.

The locking part 35 of the return actuator 31 is configured to engage with the contact trigger 14. The locking part 35 is a rectangular protrusion which extends from the return actuator 31 along the second axis. The locking part 35 extends from the other side of the return actuator 31 to the engaging part 33 and the peg 34. The locking part 35 is elongate along the first axis. The locking part 35 provides a vertically extending surface to engaging with the contact trigger 14. The locking part 35 is configured to engage with a corresponding notched portion of the contact trigger 14.

An interaction between the locking part 35 and the contact trigger 14 is shown in FIGS. 8A, 8B and 8C.

An upper surface of the contact trigger 14 is formed to have a rectangular slot 15. The shape of the contact trigger corresponds to the shape of the locking part 35. An upper section of the slot 15 may be enlarged to include an additional circular portion. FIG. 8A shows the locking part 35 engaged with the contact trigger 14. The return actuator 31 is in the first position and the contact trigger 14 is in the engaged position. The locking part 35 is in abutment with the vertical sides of the slot 15. The locking part 35 is restrained from moving along the third axis by the side wall of the slot 15. The return spring 32 pushes the locking part 35 against the side of the slot 15. The return actuator 31 is restrained from moving to the second position.

FIG. 8B shows the contact trigger 14 in the disengaged position. The contact trigger 14 is moved down with respect to the locking part 35. The locking part 35 is not in contact with the side walls of the slot 15. The contact trigger 14 is moved such that the locking part 35 is aligned with the circular portion formed in the contact trigger 14. The locking part 35 can move along the third axis. The return actuator 31 can be rotated to the second position, as shown in FIG. 8C.

The return spring 32 is configured to bias the contact trigger 14 to the disengaged position. The first end return spring 32 is fixedly attached to the contact trigger 14. The first end of the return spring 32 forms a loop around a corresponding protrusion on the surface of the contact trigger 14. The return spring 32 is attached to the contact trigger 14 at a point below the pivot point of the contact trigger 14. The return spring 32 exerts a force on the contact trigger 14 along the third axis. The return spring 32 rotates the contact trigger 14 from the engaged position to the disengaged position. The contact trigger 14 can be moved to the engaged position on contact with the skin of a patient.

Operation of the contact trigger 14 and the medicament delivery mechanism will be described in detail with respect to FIGS. 8 to 12.

FIG. 1 shows the device 10 in an initial state. The contact trigger 14 is in the disengaged position. The locking arm 43 is in the locked position. The button 42 is locked. The blocking element 41 is in the blocking position. The injection arm 21 and the needle 12 are in the retracted position. The return actuator 31 is in the first position.

Figure 8:
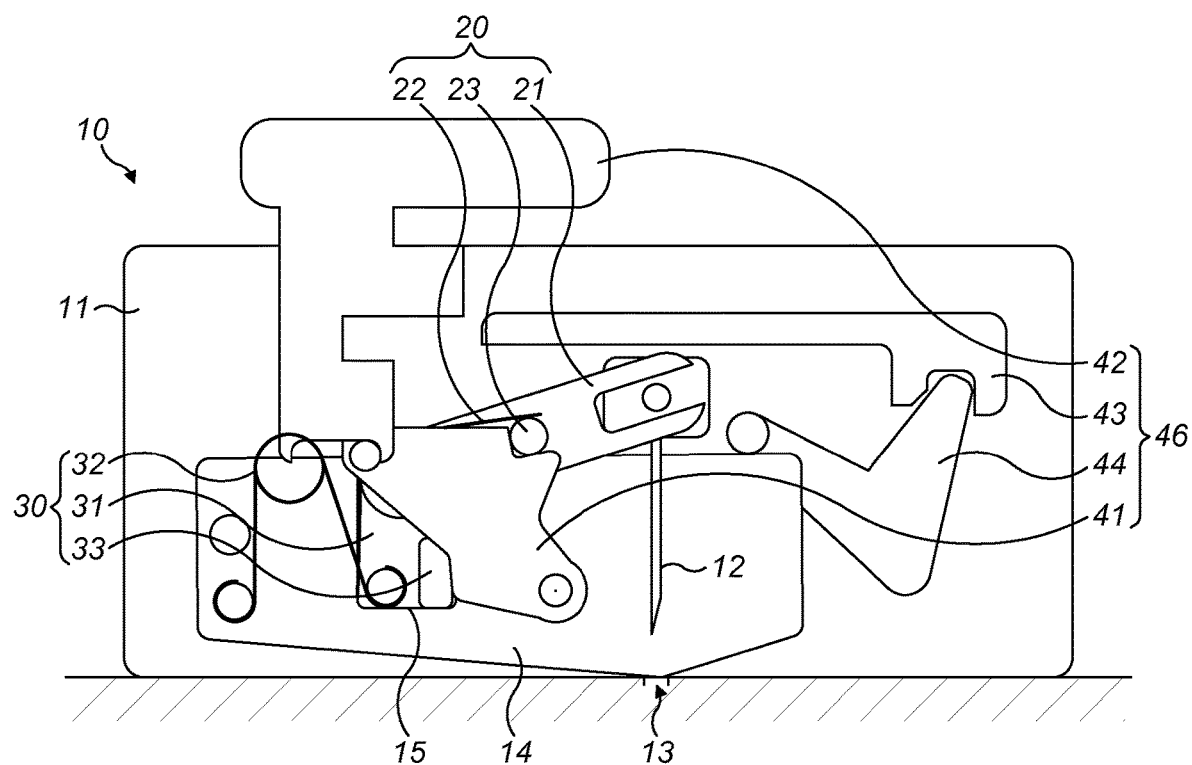
FIG. 8 is a schematic side view of the FIG. 1 injection device.

FIG. 8 shows the device 10 in an engaged state. The device 10 is shown in position on the skin of a patient. The device 10 may be placed in position by a patient themselves or by a care-giver. Contact with the skin of a patient causes the contact trigger 14 to move from the disengaged position to the engaged position.

The contact trigger 14 is engaged with the second end of the unlocking lever 44. Movement of the contact trigger 14 to the engaged position causes the unlocking lever 44 and locking arm 42 to move from the locked position to the unlocked position. The trigger mechanism 40 of the device 10 can be unlocked by movement of the contact trigger 14 to the engaged position. The trigger mechanism 40 can be unlocked by placing the lower side 11b of the device 10 in position on the skin of a patient. In the engaged state, the button 42 can be pushed by a patient or care-giver to activate the insertion mechanism 20.

The insertion mechanism 20 of the device 10 cannot be activated when the device 10 is not engaged with the skin of a patient. The device 10 avoids activation of the insertion mechanism 20 and deployment of the needle before the device 10 is properly attached to a patient. Additionally, when the contact trigger 14 is moved to the engaged position the trigger mechanism 40 can be automatically unlocked. The device 10 can provide an operation which is safer and more convenient for the patient or care-giver operating the device.

The engaging part 33 of the return actuator 31 is configured to engage with the slot 15 when the contact trigger is in the engaged position. The slot 15 is configured to prevent the return actuator 31 from moving to the second position. As shown in FIG. 8, the return actuator 31 is prevented from moving to the second position by the blocking element 41 and by the contact trigger 14.

Figure 9:
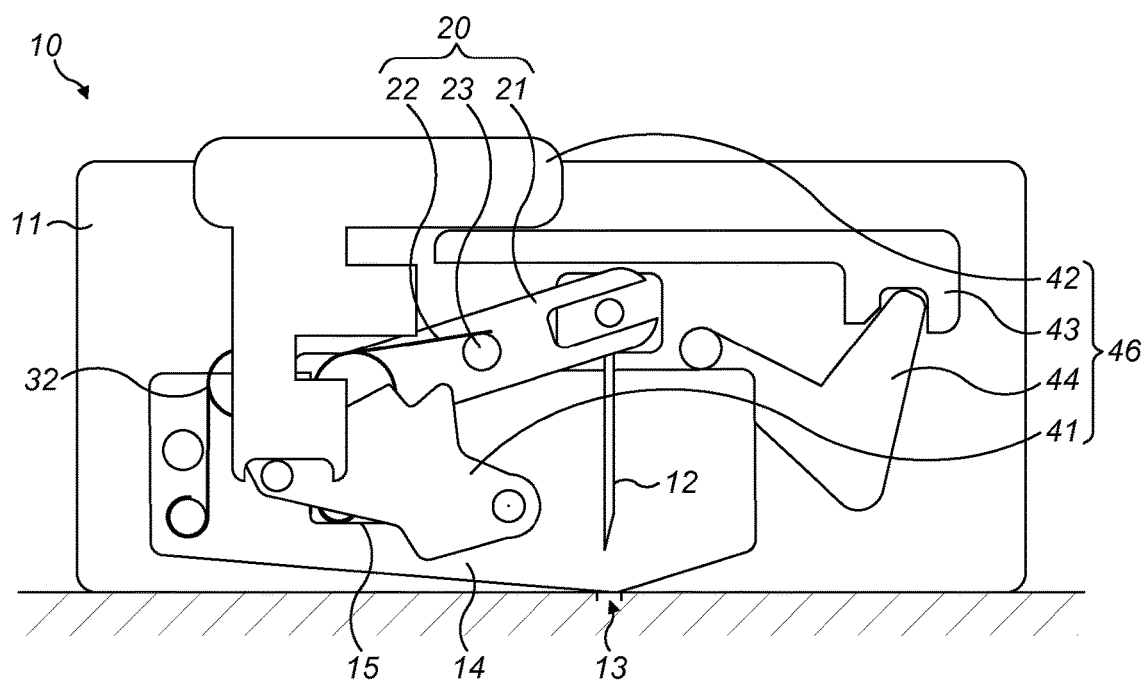
FIG. 9 is a schematic side view of the FIG. 1 injection device.

FIG. 9 shows the device 10 in a first activated state. The button 42 is pushed down. The button 42 engages with the blocking element 41 when pushed to move the blocking element 41 from the blocking position to the release position. The blocking element 41 is disengaged from the peg 23 of the injection arm 21. The injection arm 21 is free to move to the inserted position. The blocking element 41 is further disengaged from the return actuator 31. The return actuator 31 is retained in the first position by the contact trigger 14.

Figure 10:
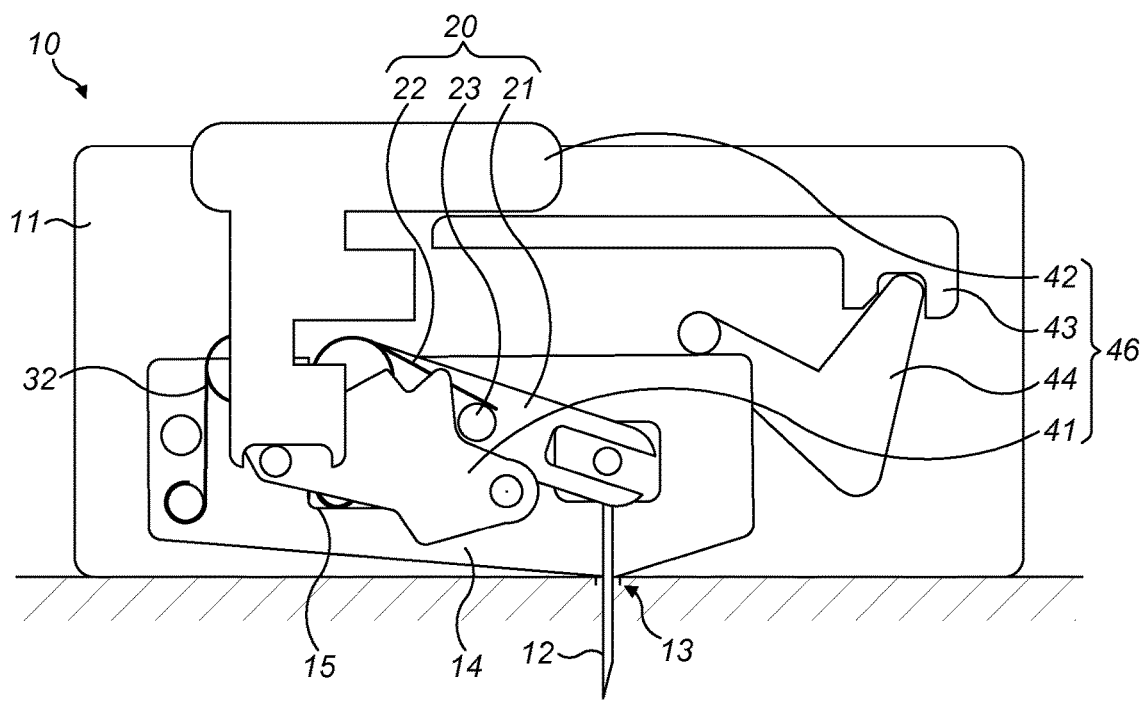
FIG. 10 is a schematic side view of the FIG. 1 injection device.

FIG. 10 shows the device 10 in a second activated state. The needle 12 is moved to the inserted position. The injection arm 21 is moved to the inserted position by the injection spring 22. The injection arm 21 pivots until the peg 23 engages with the blocking element 41. The blocking element 41 is configured to limit the movement of the injection arm 21 in the inserted position. The injection arm 21 moves the needle 12 through the aperture 13 and causes the needle 12 to be injected into the skin of a patient. Once the needle insertion mechanism 20 has been activated, the medicament delivery process can begin to delivery medicament through the needle 12. The medicament delivery process may be activated manually by a patient or care-giver.

Alternatively, the medicament delivery process may be activated automatically following the activation of the needle insertion mechanism 20.

The engaging part 33 of the return actuator 31 is disposed in the slot 15 of the contact trigger 14. The return actuator 31 is retained in the first position. When the insertion mechanism 20 has been activated, the retraction mechanism 30 can be activated according to the position of the contact trigger 14. The contact trigger 14 is configured to activate the retraction mechanism 30 when the device 10 is removed from the body of a patient.

Figure 11:
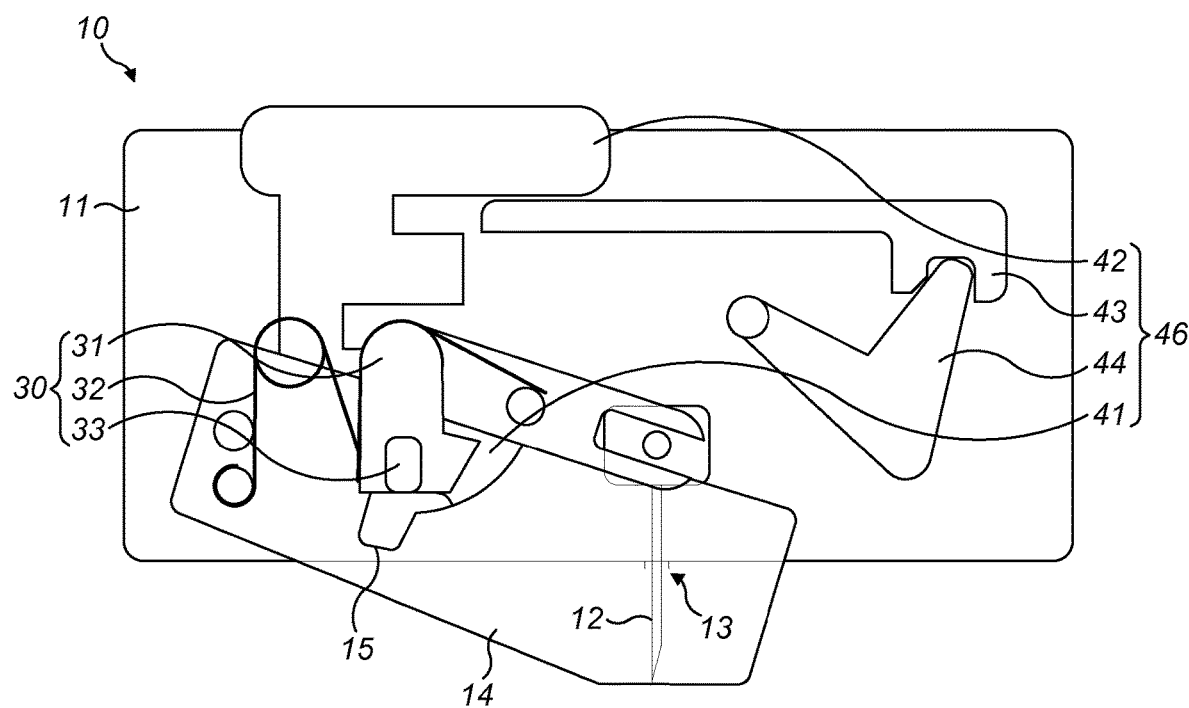
FIG. 11 is a schematic side view of the FIG. 1 injection device.

FIG. 11 shows the device 10 is a first completed state. The medicament delivery process is completed and the device 10 is detached from the skin of the patient. The contact trigger 14 is moved from the engaged position to the disengaged position by the return spring 32. The contact trigger 14 extends from the lower side 11b of the housing 11 in the disengaged position. As the device 20 is lifted away from the skin of a patient, the contact trigger 14 is maintained in contact with the skin by the return spring 32 until the disengaged position is reached. The contact trigger 14 can cover the needle 12 as the device 10 is detached from a patient. The contact trigger 14 can protect the needle 12 until the retraction mechanism 30 is activated.

In the completed state of the device 10, the engaging part 33 is disengaged from the slot 15. The return actuator 31 is free to move to the second position. The return spring 32 is configured to move the return actuator 31 to the second position. The retraction mechanism 30 can be automatically activated by the contact trigger 14 when the device 10 is detached from the skin of a patient.

Figure 12:
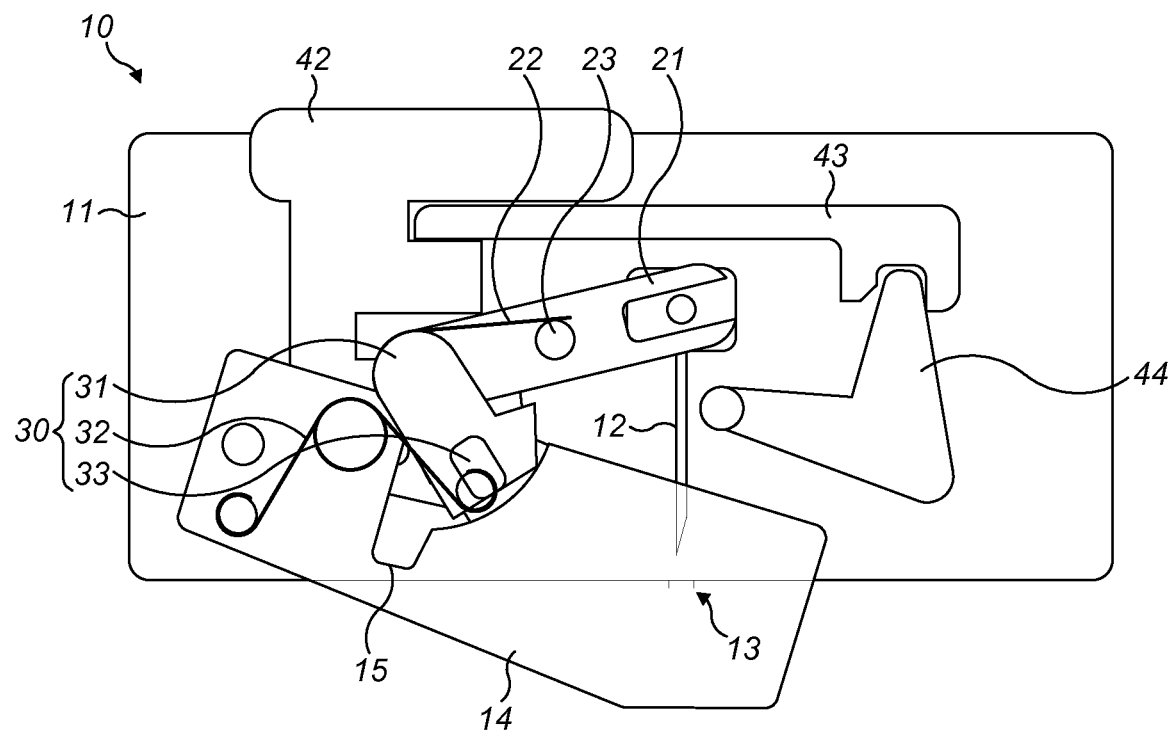
FIG. 12 is a schematic side view of the FIG. 1 injection device.

FIG. 12 shows the device 10 in a second completed state. The return actuator 31 has been moved to the second position by the return spring 32. The return actuator 31 engages with the injection arm 21 and moves the injection arm 21 to the retracted position. The needle 12 is moved to the retracted position by the retraction mechanism 30. The engaging part 33 of the return actuator 31 is arranged to engage with the contact trigger 14 when the return actuator is in the second position. The engaging part 33 is configured to prevent the contact trigger 14 from moving to the engaged position. The contact trigger 14 is maintained in the disengaged position by the engaging part 33 when the device 10 has been used. The device 10 provides a clear indication that the medicament delivery process is completed, and avoids an attempt to use the device 10 a second time.

The retraction mechanism 30 of the device 10 can be activated automatically when the contact trigger 14 moves to the disengaged position. The needle 12 can be automatically moved to the retracted position when the medicament delivery process is completed. The device 10 can avoid injury caused by exposure of the needle 12 when the device 10 is detached from a patient. The device 10 can provide an operation which is safer and more convenient for the patient or care-giver operating the device.

Although a few embodiments have been shown and described, it will be appreciated by those skilled in the art that changes may be made in these embodiments without departing from the invention, the scope of which is defined in the appended claims. Various components of different embodiments may be combined where the principles underlying the embodiments are compatible.

For example, the user activated button may be any form of user actuated input, for instance a switch or lever. The button may be an electronic touch sensor or a soft button provided on a touchscreen. The button may be a component of the needle insertion mechanism. The button may be arranged to push the needle directly from the retracted position to the inserted position. The blocking element may be slideably mounted and configured to slide from the blocking position to the release position in response to, for example, a pushing force from the button or a rotating action of a user actuated lever.

The locking arm may be arranged to engage with the blocking element to prevent movement of the blocking element from the blocking position to the release position. Alternatively, the locking arm may engage with the injection arm or the needle support directly, such that the button can be pushed with no effect until the needle insertion mechanism is unlocked. The button may include a biasing means to reset the position when pushed and released. Further alternatively, the locking arm may replace the blocking element such that the injection arm is released when the locking arm is disengaged. In this way, the needle insertion mechanism may be activated by the contact trigger.

The contact trigger may be a linear arrangement configured to move perpendicularly out of the lower side of the housing. A coil spring may be arranged to urge the contact trigger along a linear axis. Alternatively, the contact trigger may be a button or lever mounted on the lower side of the case, or may be provided by a proximity or contact sensor.

The needle insertion mechanism may be provided by a coil spring or another linear actuator, rather than the pivoting arrangement described above. A spring or linear needle driver may be mounted on the axis of the needle to drive the needle directly into the inserted position. The injection spring and return spring may be formed by any suitable biasing means, for example, a compression coil spring, a tension coil spring, a flat spring or by an elastic (e.g. rubber or polymer) element. Alternatively, the needle insertion mechanism and needle retraction mechanism may be driven by any suitable linear or rotary actuator such as a motor, an electromagnetic driver or a pneumatic or hydraulic driver.

A plurality of needles may be provided in an array for injection by the needle insertion mechanism, or a plurality of needle insertion mechanisms may be provided.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device, comprising:
a needle configured to move between a retracted position and an inserted position;
an insertion mechanism to move the needle from the retracted position to the inserted position when activated;
a locking arm which, in a locked position, is engaged with the insertion mechanism to prevent activation of the insertion mechanism and, in an unlocked position, is disengaged from the insertion mechanism;
a retraction mechanism to move the needle from the inserted position to the retracted position when activated; and
a trigger configured to move between a disengaged position and an engaged position,
wherein the trigger is arranged to be moved from the disengaged position to the engaged position when the medicament delivery device is placed on a body of a patient, and on moving from the disengaged position to the engaged position, the trigger is configured to move the locking arm from the locked position to the unlocked position,
wherein, on moving from the engaged position to the disengaged position, the trigger is configured to activate the retraction mechanism,
wherein the locking arm is slideably mounted and is pivotably coupled to an unlocking lever such that a rotation of the unlocking lever causes a sliding movement of the locking arm, and
wherein the trigger, on moving from the disengaged position to the engaged position, is configured to engage with the unlocking lever to rotate the unlocking lever, such that the locking arm is moved from the locked position to the unlocked position.

2. The medicament delivery device of claim 1, wherein the unlocking lever is pivotably mounted at a midpoint, and comprises a first end pivotably coupled to the locking arm and a second end arranged to engage with the trigger.

3. The medicament delivery device of claim 2, wherein the unlocking lever is formed having an angle at the pivot point, and is arranged such that movement of the trigger along a first direction causes a rotation of the first end, and a resulting rotation of the second end causes a sliding movement of the locking arm along a second direction different to the first direction.

4. The medicament delivery device of claim 1, wherein:
the insertion mechanism comprises a user actuator arranged to be pushed by a user to activate the insertion mechanism; and
in the locking position, an end of the locking arm is disposed within a receiving notch formed in the user actuator to prevent movement of the user actuator in a direction perpendicular to the locking arm and, in the unlocked position, the locking arm is withdrawn from the receiving notch.

5. The medicament delivery device of claim 4, wherein the insertion mechanism comprises:
a biasing means to urge the needle towards the inserted position; and
a blocking element arranged, in a blocking position, to prevent the needle from moving from the retracted position to the inserted position and arranged, in a release position, to allow the needle to move from the retracted position to the inserted position,
wherein the user actuator is arranged to urge the blocking element from the blocking position to the release position when pushed.

6. The medicament delivery device of claim 5, wherein the insertion mechanism comprises:
an injection arm pivotably mounted at one end and pivotably coupled to the needle at the other end; and
a guide member configured to restrict movement of the needle to a linear movement between the retracted position and the inserted position in response to a pivoting action of the injection arm,
wherein the blocking element in the blocking position is arranged in abutment with the injection arm to prevent movement of the needle to the inserted position.

7. The medicament delivery device of claim 6, wherein:
the blocking element is formed having a substantially triangular shape which is pivotably mounted at a first corner to rotate between the blocking position and the release position; and
a second corner of the blocking element is in abutment with the injection arm when the blocking element is in the blocking position, and the user actuator is configured to apply a force at a third corner of the blocking element when pushed.

8. The medicament delivery device of claim 6, wherein:
the biasing means comprises a coil spring fixed around the pivot of the injection arm; and
a first end of the coil spring is fixed in position, and a second end of the coil spring extends along the injection arm to push the injection arm towards the inserted position.

9. The medicament delivery device of claim 6, wherein the retraction mechanism comprises a return actuator pivotably mounted to rotate around the pivot point of the injection arm between a first position and a second position, and the return actuator in the first position is arranged to abut with the injection arm in the inserted position, and the return actuator is configured to urge the injection arm and needle to the retracted position of the needle when moved to the second position.

10. The medicament delivery device of claim 9, wherein the blocking element, in the blocking position, is engaged with the return actuator to retain the return actuator in the first position and, in the release position, is disengaged from the return actuator.

11. The medicament delivery device of claim 10, wherein:
the trigger is formed having a retaining slot; and
in the first position, the return actuator is aligned with the retaining slot, disposed within the retaining slot, and prevented from moving to the second position when the trigger is in the engaged position, and is released by the retaining slot when the trigger moves from the engaged position to the disengaged position.

12. The medicament delivery device of claim 11, wherein the return actuator, in the second position, is not aligned with the retaining slot and abuts with the trigger to prevent the trigger from moving from the disengaged position to the engaged position.

13. The medicament delivery device of claim 9, wherein the retraction mechanism comprises a biasing means to urge the return actuator towards the second position, wherein the trigger in the engaged position is configured to engage with the return actuator to retain the return actuator in the first position, and the trigger in the disengaged position is disengaged from the return actuator.

14. The medicament delivery device of claim 13, wherein the biasing means of the retraction mechanism comprises a coil spring, having a first end of the coil spring fixed in position and a second end of the coil spring in abutment with the return actuator to push the return actuator towards the second position, and wherein the coil spring is not fixed in position between the first end and second end.

15. The medicament delivery device of claim 14, wherein the trigger is pivotably mounted to rotate between the engaged position and the disengaged position, and wherein the first end of the coil spring of the retraction mechanism is fixed to the trigger to bias the trigger towards the disengaged position.

16. The medicament delivery device of claim 1, comprising an outer housing,
wherein the needle is disposed within the outer housing in the retracted position and extends out of the outer housing through a contact surface of the outer housing in the inserted position,
wherein the trigger is disposed within the outer housing in the engaged position and extends out of the outer housing through the contact surface of the outer housing in the disengaged position,
wherein the trigger in the disengaged position extends beyond the needle in the inserted position, and
wherein the trigger is configured to be moved from the disengaged position to the engaged position when the contact surface is placed against a user.

17. The medicament delivery device of claim 16, wherein a vertical extent of the outer housing, measured perpendicular to the contact surface, is smaller than a horizontal extent of the outer housing.

18. The medicament delivery device of claim 1, wherein the locking arm is configured to slide in a direction perpendicular to a direction in which the needle moves between the retracted position and the inserted position.

19. The medicament delivery device of claim 1, comprising an outer housing and a button configured to slide between a first position in which a proximal end of the button extends beyond a proximal end of the outer housing by a first distance to a second position in which the proximal end of the button extends beyond the proximal end of the outer housing by a second distance that is less than the first distance, the button being configured to releasably engage the locking arm.

20. The medicament delivery device of claim 19, wherein the button and the trigger are disposed on opposite sides of the outer housing.

* * * * *